Figure 1:
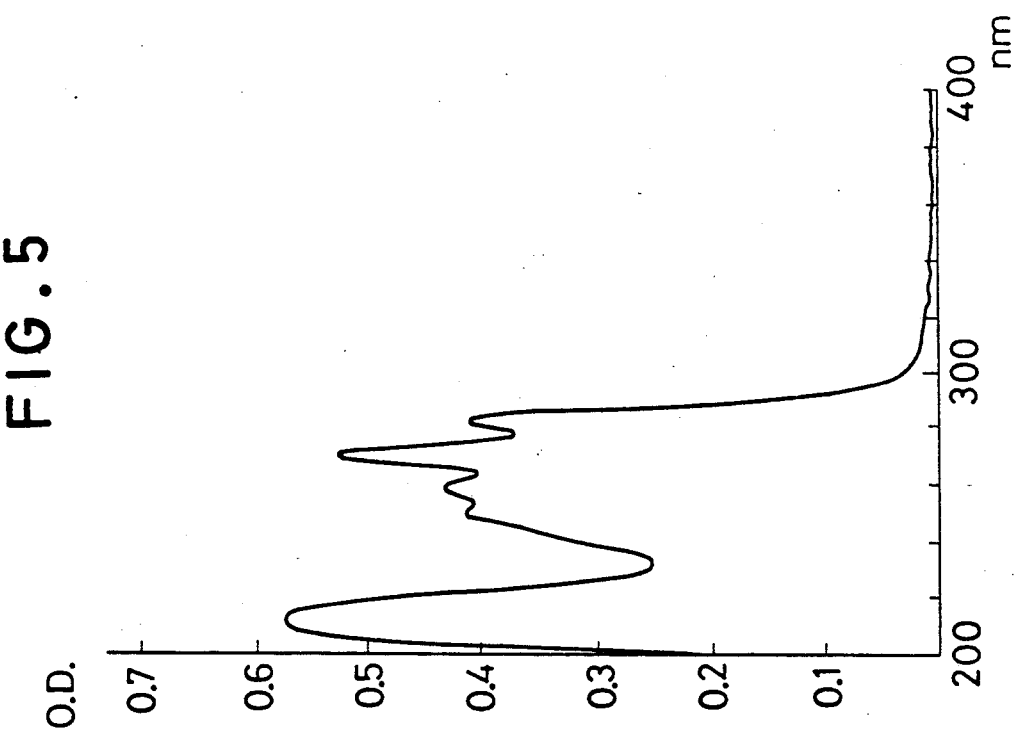

United States Patent [19]
Umezawa et al.

[11] Patent Number: 5,109,133
[45] Date of Patent: Apr. 28, 1992

[54] ANTIBIOTIC TRIENOMYCINS AND THEIR PRODUCTION

[75] Inventors: Iwao Umezawa, Tokyo; Kanki Komiyama, Yokohama, Shinii Funayama, Yokohama, all of Japan

[73] Assignee: The Kitasato Institute, Tokyo, Japan

[21] Appl. No.: 822,820

[22] Filed: Jan. 27, 1986

[30] Foreign Application Priority Data

Jan. 25, 1985 [JP] Japan .................. 60-11101
Apr. 30, 1985 [JP] Japan .................. 60-91044

[51] Int. Cl.[5] .................. C07D 225/06; C12P 17/10; A61K 31/395
[52] U.S. Cl. .................. 540/461; 435/121; 514/183
[58] Field of Search .............. 435/121, 886, 253, 169; 540/461; 514/183

[56] References Cited

U.S. PATENT DOCUMENTS 4,521,339  6/1985  Otake et al. .................. 435/121
4,649,135  3/1987  Otake et al. .................. 435/121

OTHER PUBLICATIONS

"Studies on Mycotrienin Antibiotics, a Novel Class of Asamycins", *The Journal of Antibiotics*, vol. 35, No. 11 Nov., 1982, pp. 1460-1466.
"Communications to the Editor", *The Journal of Antibiotics*, vol. 36, No. 2, Feb., 1983, pp. 187-189.

*Primary Examiner*—Douglas W. Robinson
*Assistant Examiner*—Irene Marx
*Attorney, Agent, or Firm*—Young & Thompson

[57] ABSTRACT

Novel compounds of the formula

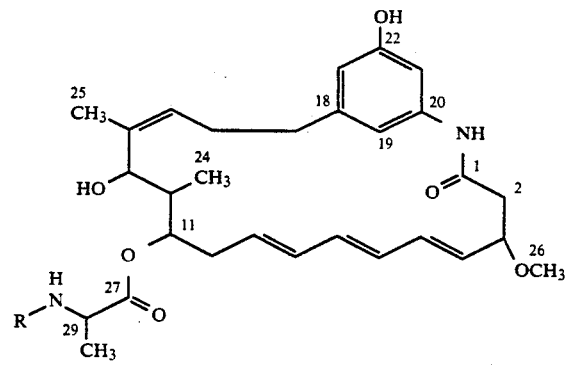

wherein R is hexahydrobenzoyl, isovaleryl or 2-methylbutyryl, and pharmaceutically acceptable salts thereof. The novel compounds designated as Trienomycins A, B and C are produced by culturing a microorganism belonging to genus Streptomyces, specifically Streptomyces sp. 82-16 FERM BP-939 in a medium, accumulating the new compounds in the medium and isolating the new compounds therefrom, and if required converted to a salt thereof. These compounds have antitumor activity and cytocidal activity.

4 Claims, 9 Drawing Sheets

ANTIBIOTIC TRIENOMYCINS AND THEIR PRODUCTION

This invention relates to novel antibiotic trienomycins and pharmaceutically acceptable salts thereof, and their production. More particularly, the present invention pertains trienomycin A, B, and C, and pharmaceutically acceptable salts thereof, and their production.

Heretofore, among mycotrienin group antibiotics produced by the genus Streptomyces, mycotrienin I and II (J. Antibiotics, 35, 1460 (1982)) or ansatrienin $A_2$ and $A_3$ (J. Antibiotics, 36, 187 (1983)) are known. These antibiotics exhibit antifungal activity against various fungi, however trienomycins shows no antifugal activity on the microorganisms tested. On the other hand, trienomycins exhibit cytocidal activities against human cultured carcinogenic cells such as HeLa $S_3$ cells in vitro, and antitumor activity against experimental tumors on mice. Furthermore, trienomycins have low acute toxicity on mice as compared with mycotrienins and no toxicity was observed when administered intraperitoneally at 100 mg/kg. A substance with such a specific effect and also low toxicity has not been known.

In the course of a screening program for novel antibiotics showing cytocidal activity, antibiotic substances designated as 83-16-a, -b, -c, which exhibit antifungal activity against some kind of fungi together with growth inhibitory activities against sarcoma-180 carcinoma cells and HeLa $S_3$ cells, were isolated from a fermentation broth of microorganism strain 83-16 isolated from a soil sample obtained in Niigata-ken, Japan. Since the prior known substances are not known, having the physico-chemical properties of these new substances, we have confirmed that the said antibiotics are novel, and have designated the same as trienomycin A, B and C, respectively.

An object of the present invention is to provide novel compounds which are antibiotic trienomycins and pharmaceutically acceptable salts thereof, and process for the production of the same.

Another object of the present invention is to provide novel antibiotics trienomycin A, B and C and pharmaceutically acceptable salts thereof, and a process for the production of the same.

A further object of the present invention is to provide antibiotic trienomycins which may be useful for medications, salts thereof, and process for the production thereof.

Figure 5:
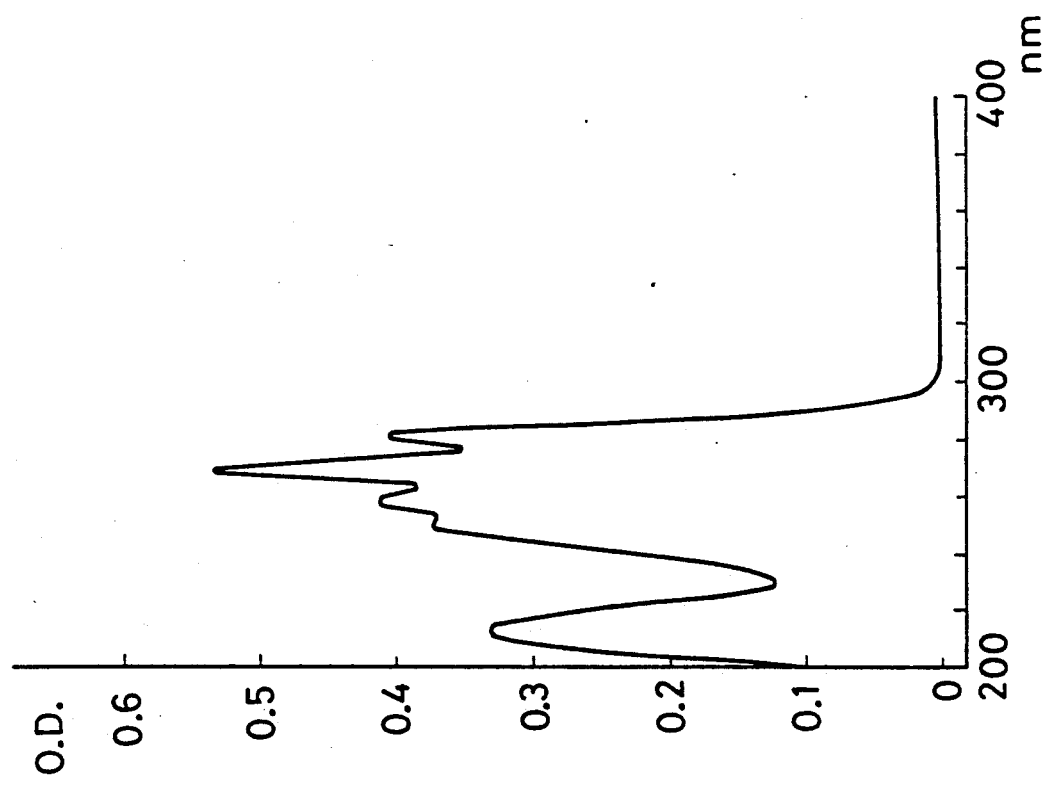
Figure 2:
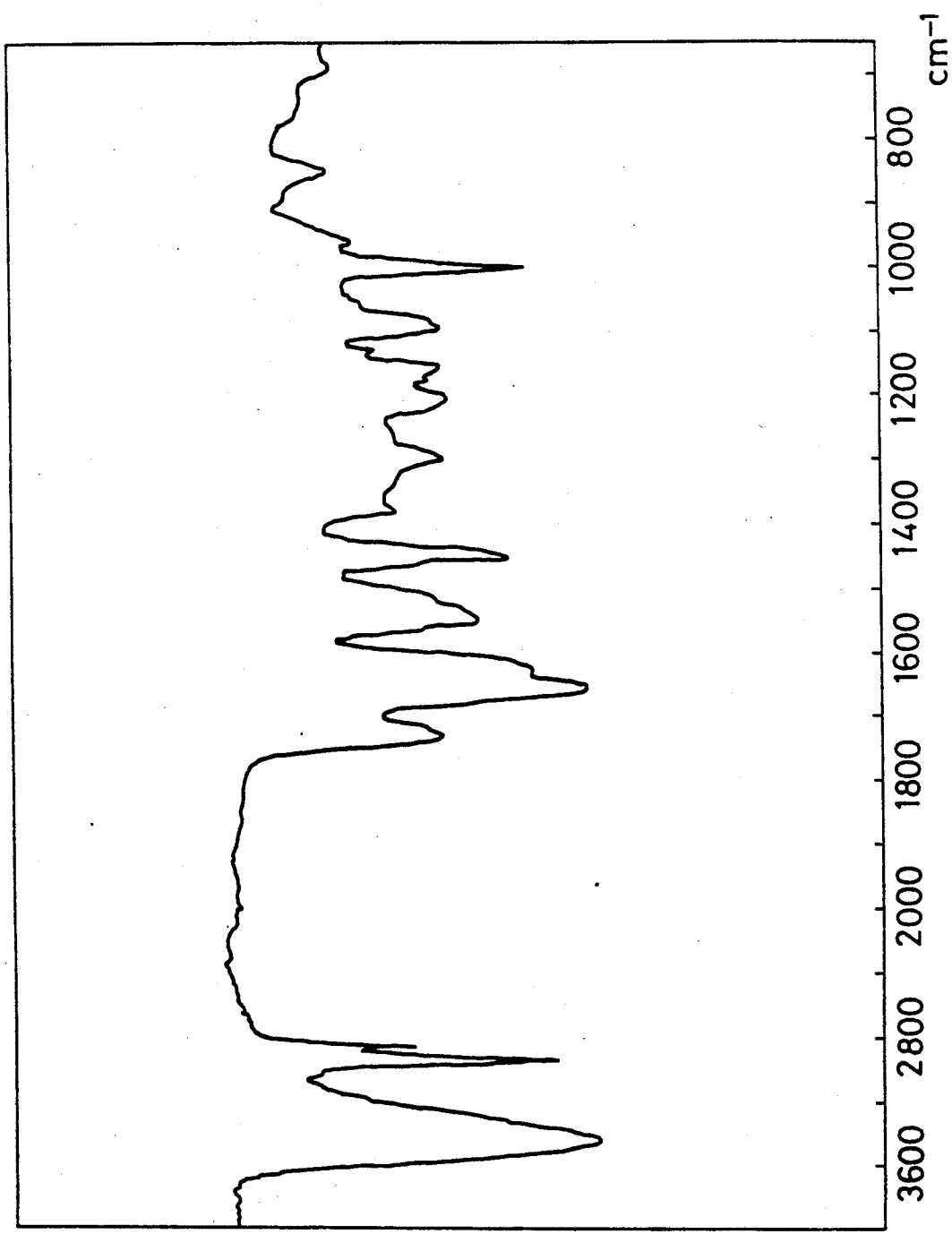
Figure 3:
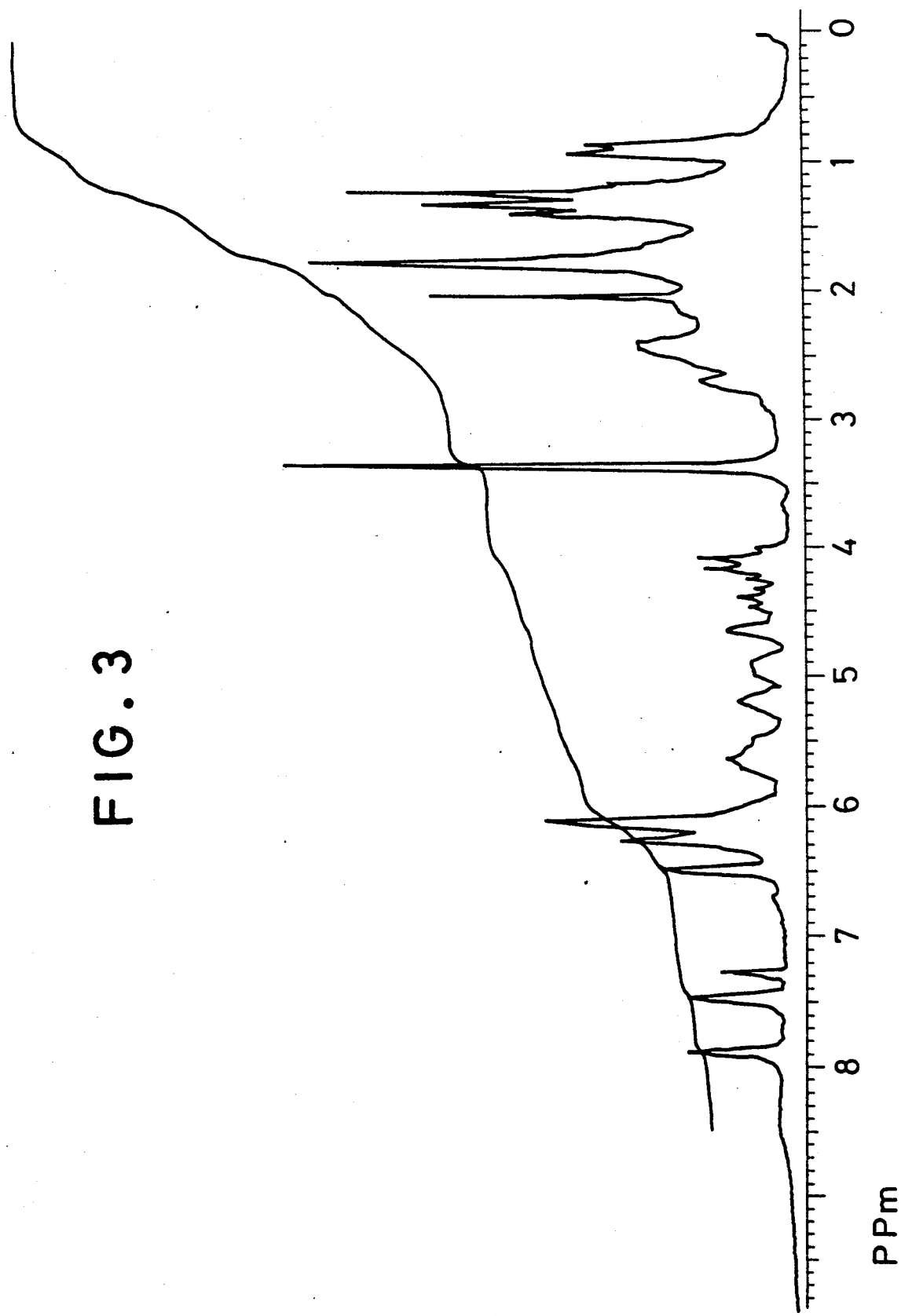
Figure 4:
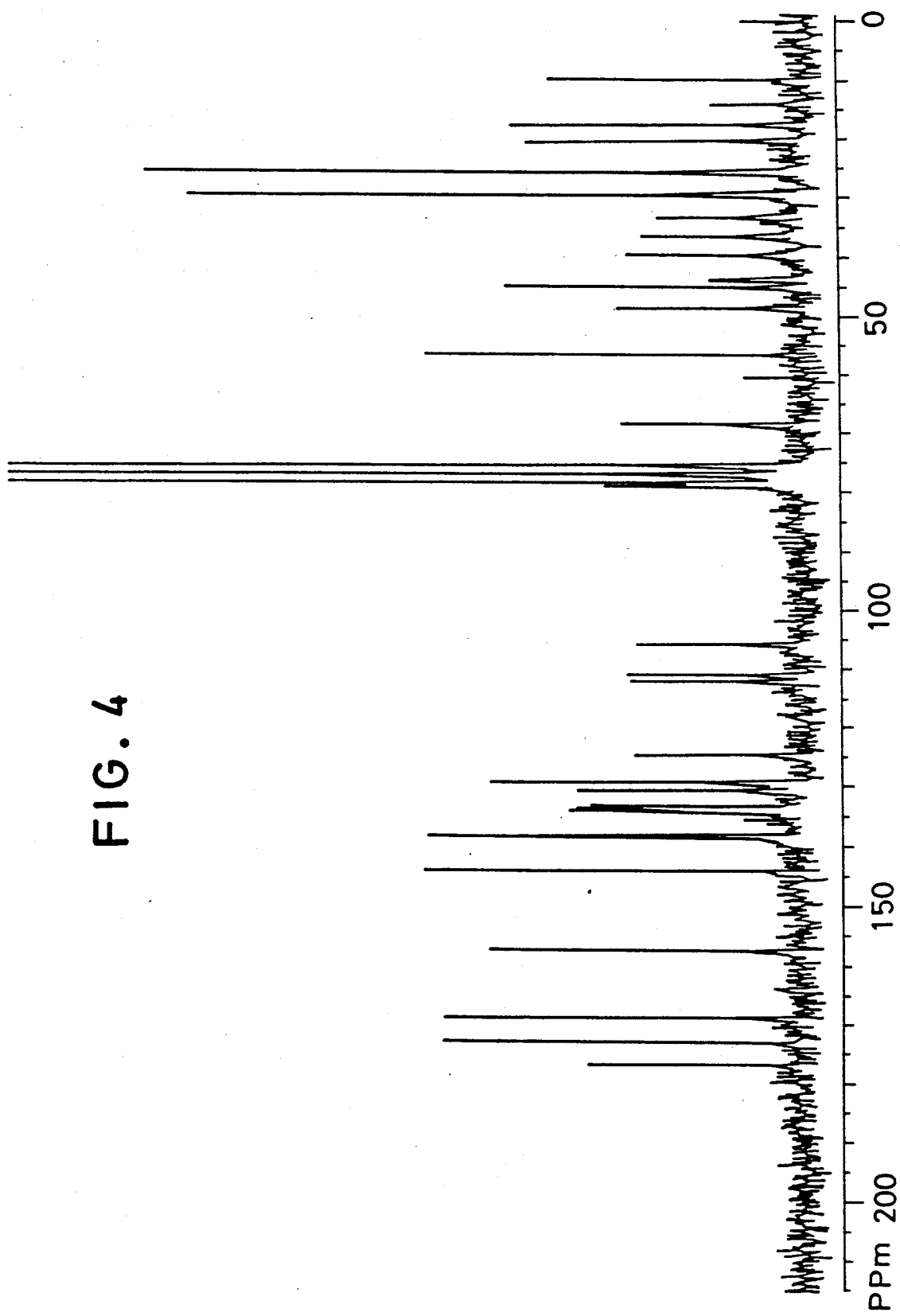
Figure 6:
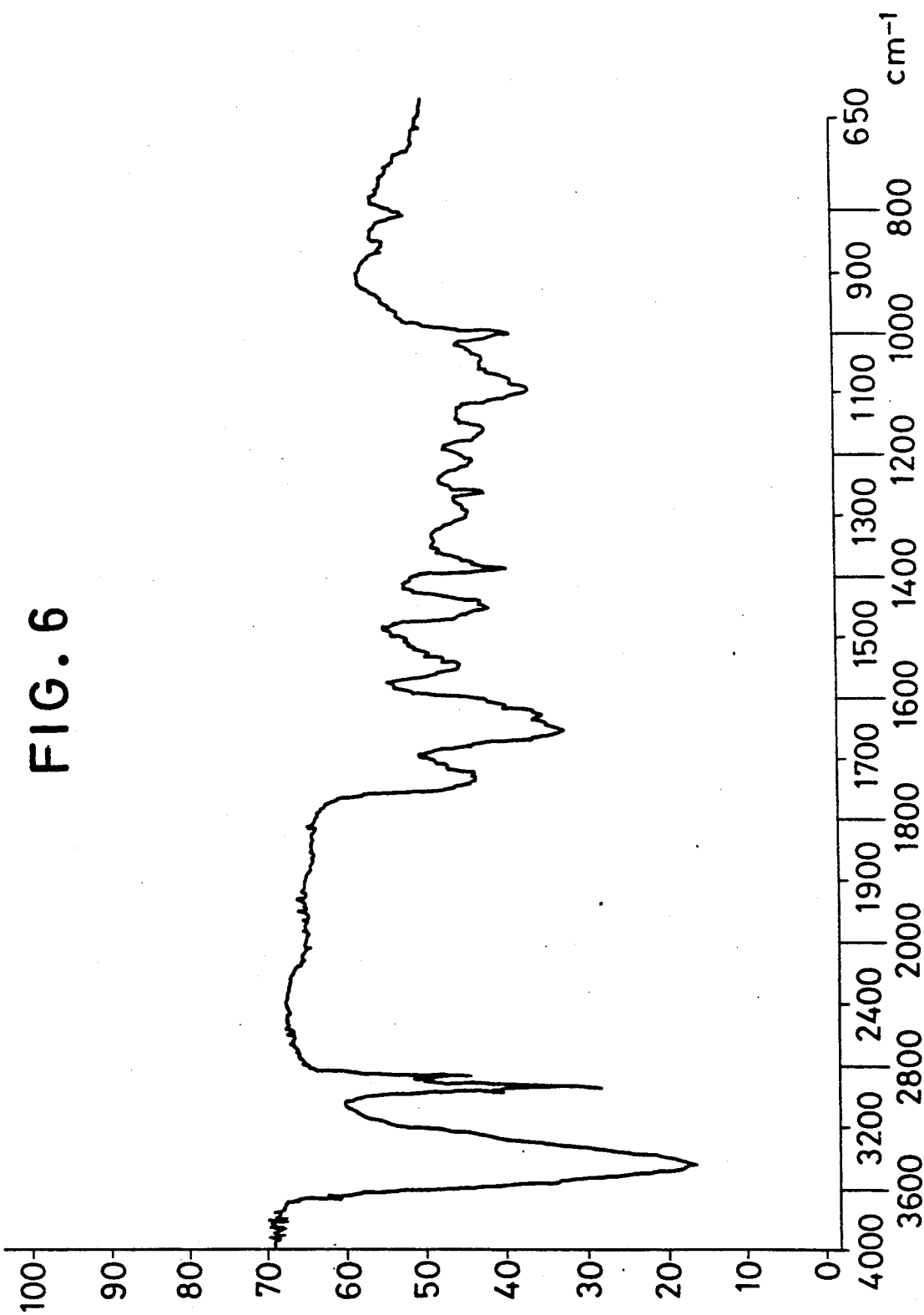
Figure 7:
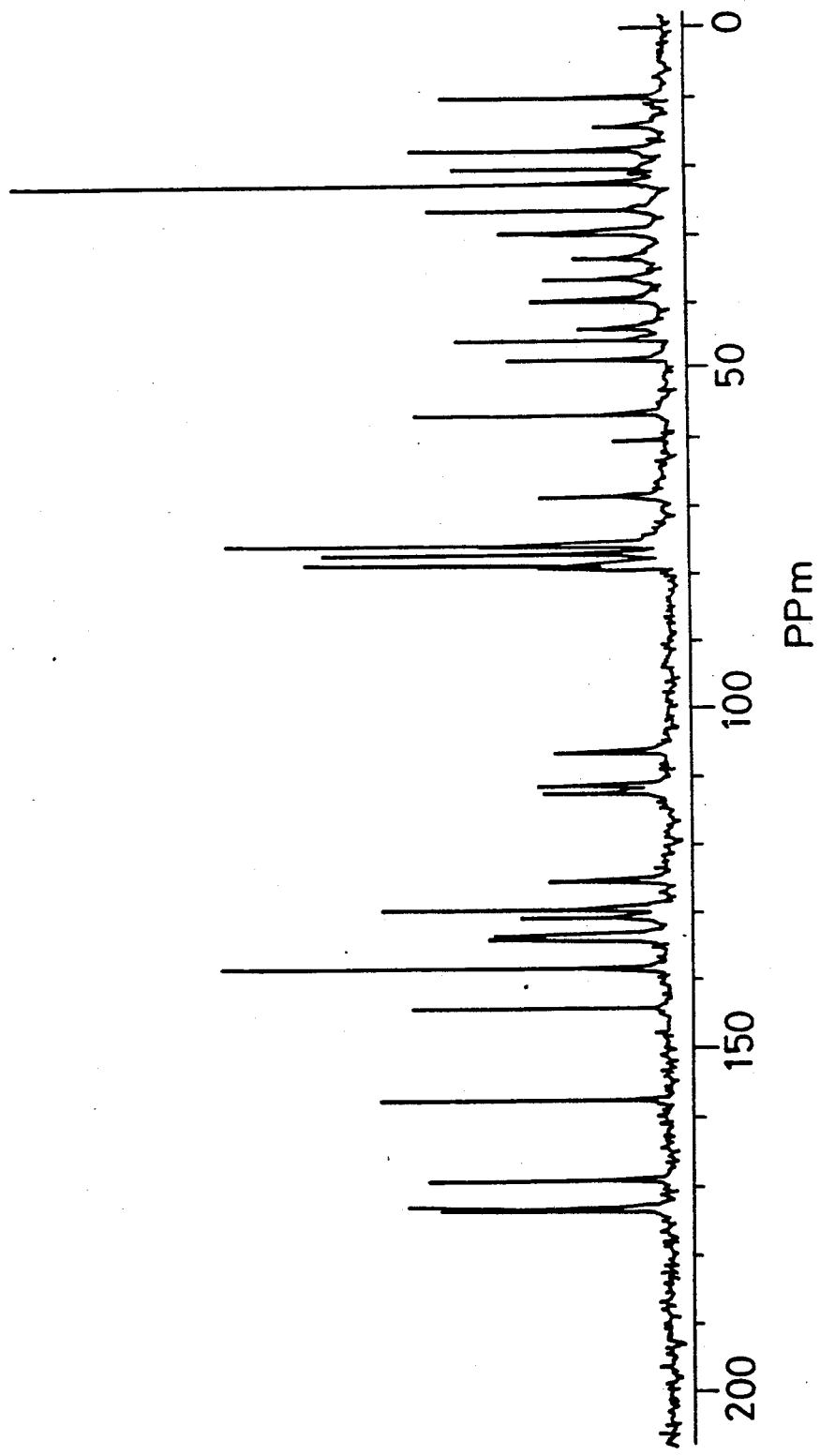
Figure 8:
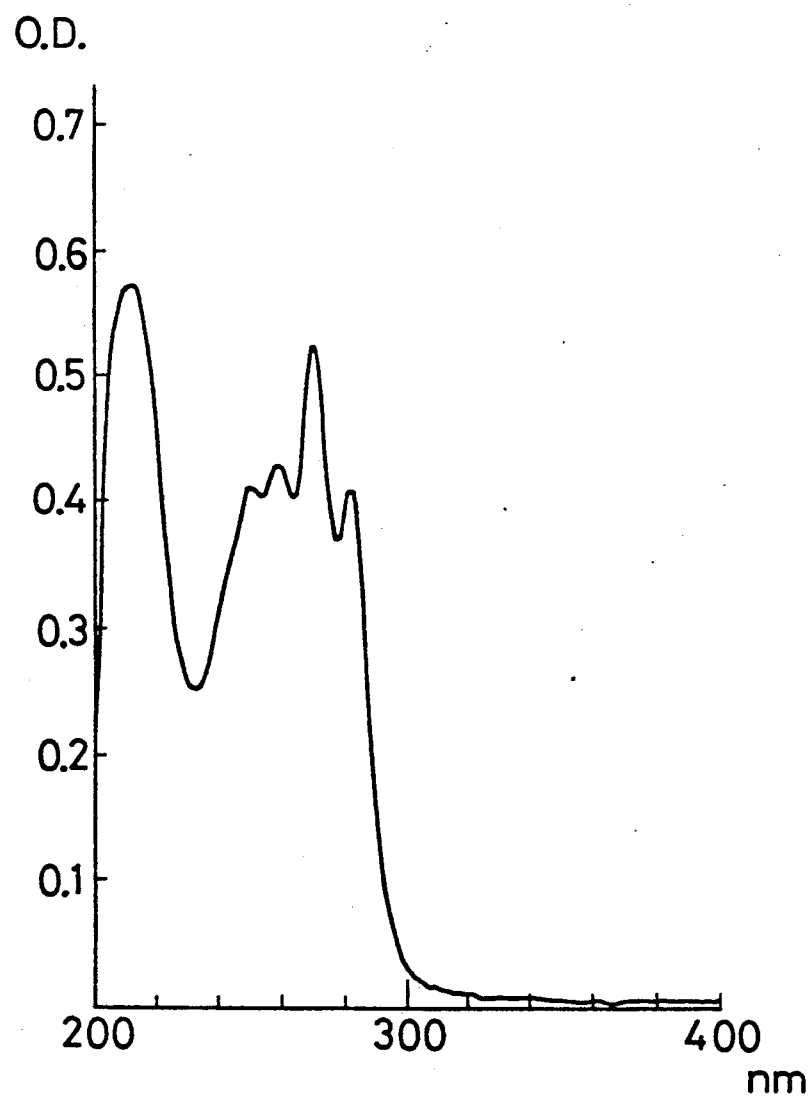
Figure 9:
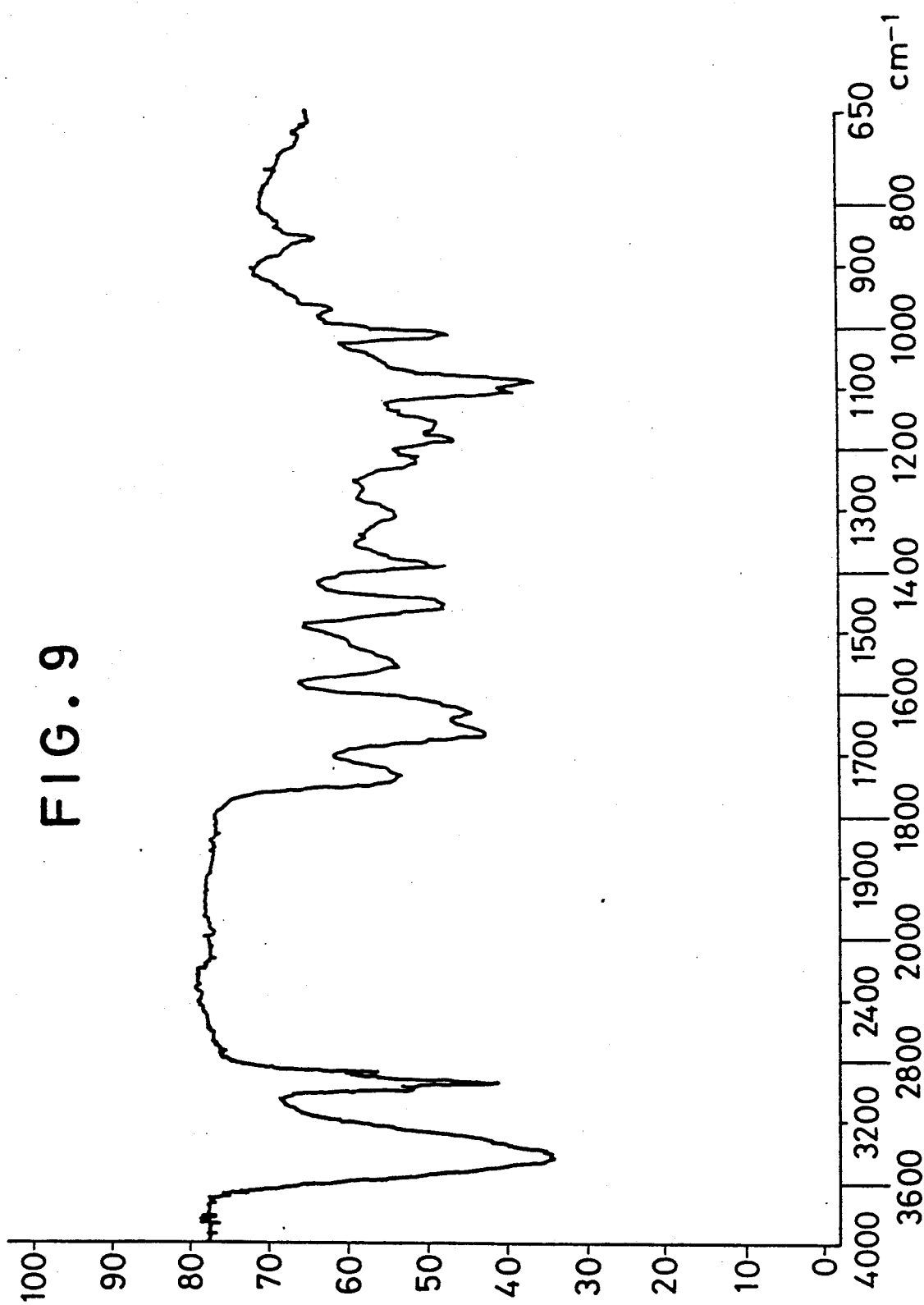
Figure 10:
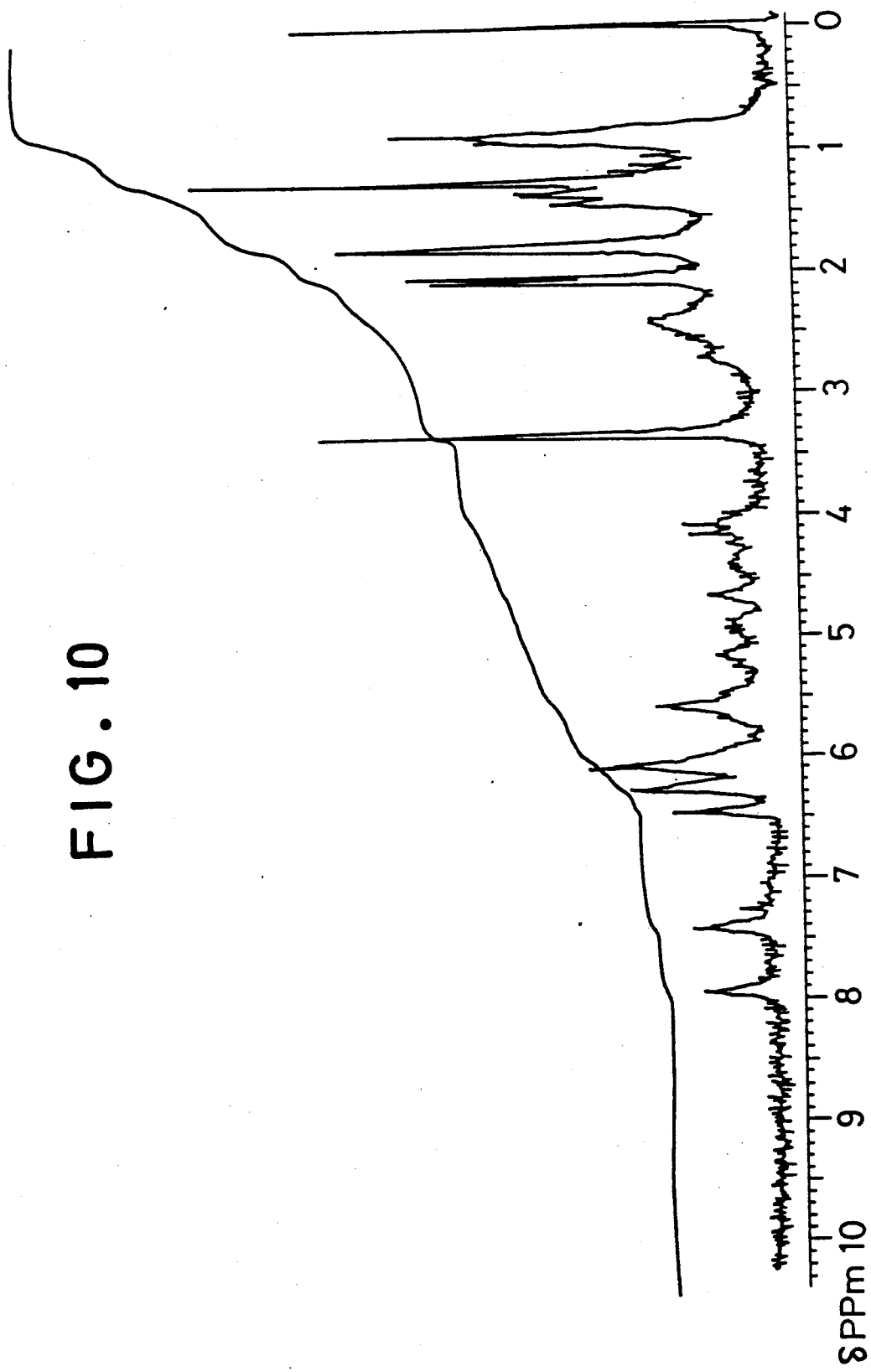

Other objects, features and advantages of the present invention will become apparent from a consideration of the following description, taken in connection with the accompanying drawings, which are graphs illustrating the present invention, and in which more particularly:

FIG. 1 is the UV-spectrum of trienomycin A;
FIG. 2 is the IR-spectrum of trienomycin A;
FIG. 3 is the $^1$H-NMR spectrum of trienomycin A;
FIG. 4 is the $^{13}$C-NMR spectrum of trienomycin A;
FIG. 5 is the UV-spectrum of trienomycin B;
FIG. 6 is the IR-spectrum of trienomycin B;
FIG. 7 is the $^{13}$C-NMR spectrum of trienomycin B;
FIG. 8 is the UV-spectrum of trienomycin C;
FIG. 9 is the IR-spectrum of trienomycin C; and
FIG. 10 is the $^{13}$C-NMR spectrum of trienomycin C.

Antibiotics trienomycin A, B and C (hereinafter sometimes generically designated as trienomycins) have the chemical structure hereinbelow illustrated, and can be produced by culturing an antibiotic trienomycins-producing microorganism belonging to the genus Streptomyces in a nutrient medium until the antibiotics are accumulated and isolating trienomycin A, B and C therefrom.

Trienomycins-producing microorganisms used in the present invention belong to the genus Streptomyces and a strain 83-16 belonging to the genus Streptomyces isolated by the present inventors is an illustration and is useful for the present invention.

The taxonomic properties of the strain 83-16 are illustrated as follows:

A. Morphological properties:

Observations of a strain on Waksman agar plate medium cultured at 27° C. for 14 days are as follows:

Mycelial growth. Substrate mycelia are not split. The aerial mycelia are irregularly branched with no vertical formation. No sporophores are observed on the top of the mycelia. The chains of spores consist of more than 20 spores and are almost straight. Most of the spores are elliptical or cylindrical and measured $0.5-0.7\times0.8-1.0$ µm in size, and the surfaces are warty.

B. Cultural properties of the strain 83-16 on various media at 27° C. for 14 days observation are shown in Table 1.

TABLE 1

| Medium | Growth | Aerial Mycelium | Reverse | Soluble Pigment |
|---|---|---|---|---|
| Tyrosin agar | Good | Brownish gray | Dark brown | Olive gray |
| Yeast extract malt Extract agar | Good | Shadowy gray | Grayish yellow Brown | Pale yellow Brown |
| Nutrient agar | Good | Shadowy gray | Beige | Chocolate brown |
| Glycerol-asparagin agar | Moderate | Beige gray | Pale yellow brown | Grayish yellow brown |
| Inorganic salts-starch agar | Moderate | Dark covert gray | Brownish gray | Grayish yellow brown |
| Oatmeal agar | Poor | Light brownish gray | Light brownish gray | Light brownish gray |
| Peptone-yeast extract-iron agar | Poor | Parchment | Light brownish gray | Chocolate brown |

C. Physiological properties of the strain 83-16:

1. Growth temperature: 20°-37° C., optimum temperature approximately 27° C.
2. Liquefaction of gelatin (glucose-peptone-gelatin medium): Doubtful
3. Starch hydrolysis (starch-inorganic salt agar medium): Negative
4. Coagulation of milk peptonization (10% skim milk medium): Doubtful
   Coagulation: Negative
5. Melanin formation (tyrosin agar medium and peptone-yeast extract-iron agar): Positive
6. Production of hydrogen sulfate (peptone-yeast extract-iron agar): Negative
7. Nitrite formation (nitrate medium): Negative D. Utilization of carbon sources (Pridham-Gottlieb agar medium at 27° C. for 1-2 months):

| Responses | Carbon Source |
|---|---|
| Positive | L-arabinose, D-xylose, D-glucose, D-fructose, inositol, L-rhamnose, |

| Responses | Carbon Source |
|---|---|
| | D-raffinose, D-mannitol |

E. Composition of cell wall:

Cell wall analysis according to the method of Becker et al. (Appl. Microbiol., 13, 236-243 (1965)) shows the presence of LL-diaminopimelic acid.

Microscopic studies and the cell wall type indicate that strain 83-16 belongs to the genus Streptomyces. This strain has been deposited in the Fermentation Research Institute, Agency of Industrial Science and Technology, M.I.T.I, Japan as No. FERM BP-939.

Since the taxonomical properties of Streptomyces are easily mutatable and are not stable, it is quite easy to mutate by means of natural or artificial mutation procedures, for example conventional ultraviolet irradiation or X-ray irradiation, or mutagens such as N-methyl-N'-nitro-N-nitrosoguanidine and ethyl methanesulfonate. Hence, artificial mutants and natural mutants belonging to the genus Streptomyces and having a property of producing antibiotic trienomycins can be used in the present invention.

In the present invention, a trienomycins-producing microorganism belonging to the genus Streptomyces is cultured in a suitable nutrient medium. A conventional medium for Streptomyces can be used. Such a medium contains assimilable carbon sources, digestible nitrogen sources for microorganisms and if required inorganic salts. Examples of assimilable carbon sources are glucose, molasses, starch, dextrin, cellulose, corn steep liquor, glycerin and organic acids, which are used in combination or alone. Examples of digestible nitrogen sources are organic nitrogen-containing compounds such as peptone, meat extract, yeast extract, dry yeast, soybean powder, corn steep liquor, cotton cake, caseine, soybean protein hydrolyzates, amino acids and urea, and inorganic nitrogen-containing compounds such as nitrates and ammonium salts which are used in combination or alone. If required, inorganic salts of sodium, potassium, calcium or magnesium can be added. Other trace nutrients, growth stimulators or precursors can optionally be added.

Cultivation can be carried out by conventional aeration culture such as shaking culture and aeration culture. For industrial production, submerged aeration culture is preferable. The pH of the culture medium is preferably neutral. The culturing temperature is 20°-37° C., generally 24°-30° C., preferably approximately 27° C. The culturing time for the accumulation of trienomycins is generally for 3-6 days using liquid culture and is preferably terminated when the maximum accumulation of antibiotics is achieved. These conditions can be selected according to the strain used and culturing conditions for maximum production of antibiotics. Also anti-foamers such as silicone oil, vegetable oil or surface active agents can be added.

Since trienomycins are accumulated in the cultured liquor, the cultured broth is filtered with an added filter-aid such as CELITE and HYFLO-SUPERCEL (trade name) or by centrifugation to separate mycelia and then the antibiotics are isolated from the filtrate.

The isolation of the antibiotics from the filtrate can be performed by making use of the weakly acidic nature of trienomycins, whereby for example they are insoluble in hexane and water and soluble in organic solvents such as methanol, ethanol, dichloromethane, chloroform, acetone and ketone. In general, trienomycins are transferred to the organic solvent layer by extracting the cultured filtrate with a water-immiscible organic solvent such as chloroform, dichloromethane, ethyl acetate or butyl acetate. Preferably, the pH of the filtrate is previously adjusted at pH 5.0-7.0.

The organic solvent layer is, if required, washed with a dilute solution of ethylenediamine tetra-acetate to remove metallic ions, and dehydrated by adding, for example anhydrous sodium sulfate or anhydrous magnesium sulfate. The dehydrated organic solvent layer is evaporated in vacuo to remove the organic solvent. The temperature of the concentration operation is preferably maintained below 60° C. to avoid decomposition of the trienomycins. The antibiotics can be precipitated by adding an organic solvent such as hexane and petroleum ether to the residue. The precipitate is washed several times with this solvent and the antibiotics can be obtained by filtration or centrifugation as a brownish crude substance.

Further purification can be achieved by making use of the difference in solubility of the antibiotics and the contaminants, the difference in distribution between two immiscible liquid phases, or the difference in adsorption on a given adsorptive carrier. Especially, chromatography is preferable for the purification of trienomycins. Preferred examples of chromatography for the purification of trienomycins are adsorption chromatography using an adsorption resin such as silica gel, alumina, activated carbon, cellulose, hydroxy-apatite and HP-20, reversed phase partition chromatography using silylated silica gel or octadecyl silylated silica gel, gel-filtration chromatography using the molecular sieve Sephadex LH-20 or Toyopearl (trade name) as the molecular sieve, and ion-exchange chromatography using DEAE-cellulose, DEAE-Sephadex or DEAE-Toyopearl.

The trienomycins can be isolated and purified by techniques such as chromatography, electrophoresis, countercurrent distribution, ultrafiltration and distillation, in combination or alone. For example, a crude substance is dissolved in small amount of chloroform or benzene, adsorbed on a previously packed silica-gel column, chromatographed with a mixed solvent of benzene-acetone to collect the active fractions and concentrated in vacuo. Then the concentrate is dissolved in a small amount of chloroform and is adsorbed on a silica-gel column, chromatographed with a mixed solvent of chloroform-methanol and concentrated the active fractions in vacuo. The residue is dissolved in a small amount of methanol, charged on a reversed phase silica-gel column and eluted with a mixed solution of methanol and water to separate trienomycins A, B and C.

The thus-obtained trienomycins A, B and C are weak acidic substances, and the pharmaceutically acceptable salts thereof such as the sodium salt, calcium slat and magnesium slat can be prepared by conventional means.

The physico-chemical properties of trienomycins A, B and C are illustrated in Table 2.

Among known antibiotics similar to trienomycins A, B and C, mycotrienin I (ansatrienin A), mycotrienin II (ansatrienin B), ansatrienin $A_2$, ansatrienin $A_3$ and ansatrienone A are known, and their empirical formulae and molecular weights are given in Table 3.

TABLE 2

| | Trienomycin A | Trienomycin B | Trienomycin C |
|---|---|---|---|
| Molecular formula: | $C_{36}H_{50}N_2O_7$ | $C_{34}H_{48}N_2O_7$ | $C_{34}H_{48}N_2O_7$ |
| Molecular weight: | 622 | 596 | 596 |
| Melting point: | 131° C. (128–132° C.) | 125° C. (124–126° C.) | 120.5° C. (119.5–121.5° C.) |
| $(\alpha)_D^{20}$ (c = 0.1, methanol): | +174° | +170° | +186° |
| UV spectrum (in methanol): $\lambda_{max}^{MeOH}$ (nm) | 250, 260, 271 and 282 (FIG. 1) | 250 ($\xi^*$ = 29100) 260 ($\xi$ = 30780) 271 ($\xi$ = 37500) 282 ($\xi$ = 29000) (FIG. 5) | 250 ($\xi^*$ = 28300) 260 ($\xi$ = 28950) 271 ($\xi$ = 34800) 282 ($\xi$ = 26900) (FIG. 8) |
| IR spectrum: (KBr) | FIG. 2 | FIG. 6 | FIG. 9 |
| Solubility: | Insoluble: hexane, water Soluble: chloroform, dichloromethane, tetrahydrofuran, ethyl acetate butyl acetate, acetone, methanol, ethanol | | |
| Color reaction: | Positive: iode, $H_2SO_4$ Negative: ninhydrin, Dragendorff, ferric chloride | | |
| Nature: | weakly acidic substance | weakly acidic substance | weakly acidic substance |
| Appearance: | Colorless powder | Colorless powder | Colorless powder |
| $^1$H-NMR (CDCl$_3$, TMS): | FIG. 3 | — | — |
| $^{13}$C-NMR (CDCl$_3$m TMS): | FIG. 4 | FIG. 7 | FIG. 10 |
| Mass spectrum (m/z): (EI-MS method) | 622, 604, 590, 572, 423, 405, 391, 373, 199, 155, 111, 83 | 596, 578, 564, 560, 423, 405, 391, 373, 85, 57 | 596, 578, 564, 560, 423, 405, 391, 373, 83, 44 |
| TLC (silica-gel)(Rf): | | | |
| CHCl$_3$–MeOH (9:1): | 0.47 | — | — |
| CHCl$_3$–MeOH (19:1): | 0.26 | 0.28 | 0.28 |
| toluene-acetone: (6:4) | 0.31 | 0.48 | 0.48 |
| benzene-ethyl acetate: (1:1) | 0.24 | — | — |
| Stability: | Stable: acidic condition at ambient temperature Instable: alkaline condition over pH 10 | | |
| Chemical structure: | | | |

As shown in Table 3, the physico-chemical properties of these antibiotics are different from the trienomycins.

The biological properties of the trienomycins are as follows:

1) Antimicrobial activities:

Minimum inhibitory concentration (MIC) is illustrated in Table 4.

TABLE 3

| Trienomycin A | $C_{36}H_{50}N_2O_7$ | 622 | Ansatrienin A | $C_{36}H_{48}N_2O_8$ | 636 |
| Trienomycin B | $C_{34}H_{48}N_2O_7$ | 596 | Ansatrienin B | $C_{36}H_{50}N_2O_8$ | 638 |
| Trienomycin C | $C_{34}H_{48}N_2O_7$ | 596 | Ansatrienin A$_2$ | $C_{34}H_{46}N_2O_8$ | 610 |
| Mycotrienin I | $C_{36}H_{50}N_2O_8$ | 638 | Ansatrienin A$_3$ | $C_{34}H_{46}N_2O_8$ | 610 |
| Mycotrienin II | $C_{36}H_{50}N_2O_8$ | 638 | Ansatrienone A | $C_{36}H_{46}N_2O_8$ | 634 |

TABLE 4

| | Inhibitory zone (mm) at 1 mg/ml | | |
|---|---|---|---|
| Organism | Trienomycin A | Trienomycin B | Trienomycin C |
| Bacillus subtilis PCI 219 | — | — | — |
| B. cereus IFO 3001 | — | — | — |
| Micrococcus luteus ATCC 9341 | — | — | — |
| Staphylococcus aureus FDA 209 P | — | — | — |
| Salmonella typhimurium KB 20 | — | — | — |
| Shigella flexneri E 20 | — | — | — |
| S. sonnei E-33 | — | — | — |
| Escherichia coli | — | — | — |

TABLE 4-continued

| Organism | Inhibitory zone (mm) at 1 mg/ml | | |
|---|---|---|---|
| | Trienomycin A | Trienomycin B | Trienomycin C |
| NIHJ | — | — | — |
| *Klebsiella pneumoniae* PCI 602 | | | |
| *Enterobacter aerogenes* IAM 1183 | — | — | — |
| *Proteus vulgaris* IFO 3167 | — | — | — |
| *Candida albicans* KF 1 | — | — | — |
| *Saccharomyces sake* KF 26 | — | — | — |
| *Schizosaccharomyces pombe* IAM 4863 | — | — | — |
| *Rhizopus javanicus* IAM 6241 | — | — | — |
| *Apergillus niger* ATCC 6275 | — | — | — |
| *Alternaria kikuchiana* KF 185 | — | — | — |
| *Mucor racemosus* IFO 5403 | — | — | — |
| *Piricularia oryzae* KF 180 | (20) | (15) | (12) |

—: No inhibition. (>100 μg/ml)
The numbers in parenthesis indicate an incomplete inhibitory zone.

2) Cytocidal action on HeLa $S_3$ cells:

HeLa $S_3$ cells, $4 \times 10^4$ cells, are cultured for two days in a cell incubator, and trienomycins A, B and C are added thereto, then incubated further for three days and the cells are counted. The 50% lethal values of trienomycins A, B and C are 0.07 μg/ml, 0.25 μg/ml and 0.12 μg/ml, respectively. Furthermore, the addition of trienomycin A at a concentration of 1.0 μg/ml, and 2.0 μg/ml for trienomycin B and C, resulted in the death of the HeLa $S_3$ cells.

3) Antitumor activities:

Trienomycin A, B or C is administrated intraperitoneally in sarcoma-180-carcinoma-bearing ICR mice for 1-5 days and 7-11 days. The life prolongation effects are observed as shown in the following:

| | Life Prolongation Ratio (%) | |
|---|---|---|
| Dose (mg/kg/day) | 10 | 20 |
| Trienomycin A | 33% | 76% |
| Trienomycin B | 45% | 80% |
| Trienomycin C | 50% | 110% |

As explained hereinabove, trienomycins are expected to be useful antitumor antibiotics.

The following examples illustrate the embodiments of the present invention but are not to be construed as limiting the invention:

EXAMPLE 1

Cultivation of strain 83-16:

A loopful of cells of Streptomyces sp. 83-16 FERM BP-939 grown on an agar slant comprising glucose 1.0%, peptone 0.5%, meat extract 0.5%, NaCl 0.3% and agar 1.2%, for 14 days at 27° C. was inoculated in a sterilized liquid medium (A-medium) (pH 7.0, 100 ml) containing glucose 2.0%, peptone 0.5%, meat extract 0.5%, dry yeast 0.3%, NaCl 0.5%, and calcium carbonate 0.3%, and cultured by shaking reciprocally at 120 rpm with 17 cm amplitude, at 27° C. for 72 hours to obtain seed culture. The seed culture (2.5 l) was inoculated into sterilized A-medium (120 l) in a 200 l tank and cultured at 28° C., with aeration (60 l/min), for 3 days with agitating to obtain cultured filtrate (110 l).

EXAMPLE 2

Extraction of trienomycins:

Hyflo-supercel (5 kg) was added to the cultured filtrate obtained in Example 1 and the mixture was filtered by suction. The filtrate (105 lit.) was adjusted to pH 6 by adding 6 N-HCl. Ethyl acetate (60 lit.) was added thereto and the mixture was stirred to transfer the trienomycins into the ethyl acetate layer. After the aqueous layer and the ethyl acetate layer were separated, ethyl acetate (60 lit.) was added to the aqueous layer to transfer the trienomycins thereto. The combined ethyl acetate layer was concentration in vacuo to about 4 lit. volume. The concentrate was washed with deionized water (2 lit.), and anhydrous sodium sulfate was added to the organic solvent layer for dehydration. Then the solvent was removed in vacuo to obtain an oily material (approx. 30 g) containing trienomycins.

EXAMPLE 3

Purification of the trienomycins by silica-gel chromatography:

The oily material obtained in Example 2 was charged on a column (4.6×60 cm) of silica-gel 60 (Merk) and eluted with solvents which were continuously changing from benzene to acetone. The fractions showing cytocidal activities on HeLa cells were collected and concentrated in vacuo. The residue was charged on a column of silica gel previously packed with chloroform, and chromatographed with gradient elution from chloroform to chloroform-methanol (1:1). The active fractions were concentrated in vacuo to obtain crude trienomycins (200 mg, purity approx. 50%).

EXAMPLE 4

Isolation of trienomycin A:

The crude trienomycins were subjected to purification by high performance liquid chromatography (HPLC) or preparative thin layer silica-gel chromatography. In HPLC, the following equipment was used:
pump: TRIROTAR-V (Nihon Spectrometer Co.)
detector: UVIDEC-100-V (Nihon Spectrometer Co.)
column: octadecylsilylated silica-gel YMC packed column A-324 (Yamamura Chem. Inst., 10×300 mm).

The crude trienomycins (5 mg) obtained in Example 3 dissolved in methanol (100 μl) were injected and developed with a mixed solution of water-methanol (36:64). A peak corresponding to trienomycin A was collected by detecting with ultraviolet absorbency at 272 nm. Methanol was removed in vacuo, chloroform was added to the residue to transfer trienomycin A into the chloroform layer. The chloroform layer was washed with deionized water, dehydrated with anhydrous sodium sulfate, then concentrated in vacuo to obtain purified trienomycin A (2.0 mg).

Crude trienomycin A (20 mg) dissolved in a small amount of chloroform was streakly spotted on a preparative thin layer chromatography plate (silica-gel 60 $F_{254}$, 20×20 cm (Merk)) and developed with a mixture of chloroform and methanol (19:1). Spots of trienomycin A detectable under an ultraviolet lamp were scratched off. The silica gel thus obtained was extracted with acetone and dried in vacuo to obtain purified trienomycin A (9 mg).

EXAMPLE 5

Purification of Trienomycins B and C:

A crude sample (5 mg) obtained in Example 3 dissolved in methanol (100 μl) was injected and eluted with a mixed solution of water and methanol (40:60). Peaks corresponding to trienomycin B and C were collected by detecting with ultraviolet absorbency at 272 nm. Each fraction was concentrated in vacuo to remove methanol, and chloroform was added thereto to transfer trienomycin B or C. The chloroform layers were washed with deionized water, dehydrated with anhydrous sodium sulfate, then concentrated in vacuo to obtain purified trienomycins B and C (2 mg).

From a consideration of the foregoing disclosure, therefore, it will be evident that the initially recited objects of the present invention have been achieved.

Although the present invention has been described and illustrated in connection with preferred embodiments, it is to be understood that modification and variations may be resorted to without departing from the spirit of the invention, as those skilled in this art will readily understand. Such modifications and variations are considered to be within the purview and scope of the present invention as defined by the appended claims.

What is claimed is:

1. A compound of the formula

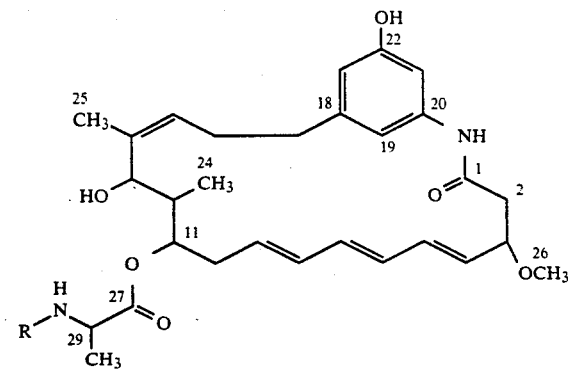

wherein R is hexahydrobenzoyl, isovaleryl or 2-methylbutyryl, or a pharmaceutically acceptable salt thereof.

2. Trienomycin A according to claim 1, wherein R is hexahydrobenzoyl.

3. Trienomycin B according to claim 1, wherein R is isovaleryl.

4. Trienomycin C according to claim 1, wherein R is 2-methylbutyryl.

* * * * *